United States Patent [19]

Tsuto et al.

[11] 4,097,242
[45] Jun. 27, 1978

[54] SULFONATION APPARATUS

[75] Inventors: Keiichi Tsuto; Kanji Majima; Shigeyasu Imamura, all of Wakayama, Japan

[73] Assignee: Kao Soap Co., Ltd., Tokyo, Japan

[21] Appl. No.: 789,873

[22] Filed: Apr. 22, 1977

Related U.S. Application Data

[62] Division of Ser. No. 704,613, Jul. 12, 1976, Pat. No. 4,086,256.

[30] Foreign Application Priority Data

Jul. 21, 1975  Japan .................................. 50-89069

[51] Int. Cl.² ........................ C07C 143/24; B01J 1/00; F28D 7/12
[52] U.S. Cl. ...................................... 23/283; 23/284; 23/285; 23/260; 260/505 S; 260/459 R; 165/130; 165/141; 165/140; 261/146
[58] Field of Search ................. 23/283, 284, 285, 260; 260/505 S, 459 R; 165/130, 141, 140; 261/146, 147

[56] References Cited

U.S. PATENT DOCUMENTS 3,270,038  8/1966  Marshall et al. ................... 23/285 X
3,891,689  6/1975  Pryce ........................... 260/505 S X Primary Examiner—James H. Tayman, Jr.
Attorney, Agent, or Firm—Blanchard, Flynn, Thiel, Boutell & Tanis

[57] ABSTRACT

A sulfonation apparatus comprising a plurality of vertical first-stage reaction tubes in which the sulfonatable material and an $SO_3$-containing gas are flowed upwardly from the lower ends thereof and a single vertical second-stage reaction tube in which the reaction products from the upper ends of all of the first-stage reaction tubes are combined and are flowed downwardly together with fresh $SO_3$-containing gas in order to complete the sulfonation reaction.

7 Claims, 2 Drawing Figures

SULFONATION APPARATUS

This is a division of application Ser. No. 704,613 filed July 12, 1976, now U.S. Pat. No. 4,086,256.

BACKGROUND OF THE INVENTION

1. Field of the Invention

This invention relates to an apparatus for the sulfonation and sulfation of organic compounds that are liquid at ordinary or reaction temperatures, including such compounds as alcoholic compounds, compounds having sulfonatable double bonds, aromatic hydrocarbons and the like.

The term "sulfonating" as used hereinafter in the specification and claims is sometimes used in a generic sense as applying to both true sulfonation and sulfation, and sometimes in a specific sense to mean true sulfonation. The term "sulfonating" or derivatives thereof is to be construed generically, unless the context in which the term is used requires the specific sense.

More specifically, the present invention relates to an improved apparatus for sulfonation wherein the above-mentioned liquid organic compounds are reacted with sulfur trioxide gas diluted with air or other inert gas.

2. Description of the Prior Art

Reactions using concentrated sulfuric acid, fuming sulfuric acid or chlorosulfonic acid as a sulfonation reagent have conventionally been practiced in a liquid-liquid mixture system and most of them are batch processes that use a large amount of the sulfonation reagent. These processes, however, are not free from various disadvantages, such as, the quality of the reaction product varies from batch to batch and/or the reaction product contains a considerably amount of unwanted inorganic compounds.

In recent years, sulfur trioxide ($SO_3$) has achieved wide use as a sulfonation and sulfation agent. Continuous liquid-gas phase reactions have been attempted and employed on a commercial scale using $SO_3$. However, the conventional reaction processes using $SO_3$, such as those mentioned below, entail various problems in production engineering.

For example, a pipe-system reactor, as disclosed in U.S. Pat. No. 2,923,728, Japanese Patent Publication No. 37407-72, Japanese Patent Publication No. 8087-73, etc., is suited for limited production rates, but it is not suitable for mass production. In order to obtain a large amount of sulfonated reaction product by the use of a single reaction tube, the diameter of the reaction tube must be made very large. It is difficult, however, to make the diameter of the reaction tube extremely large because it is difficult to achieve adequate cooling (reaction heat removing) that is critically required and for other reasons. When plural reaction tubes are disposed in parallel arrangement, strict control of the liquid-gas ratio is required for each reaction tube and hence this process is not advantageous industrially.

Japanese Patent Publication No. 37407-72 discloses a process wherein a liquid film of a sulfonatable organic liquid is raised by means of an $SO_3$-containing gas. In this proposal, the quantity of the liquid fed in can be increased substantially, in proportion to the square of the diameter of the tube, but the cooling area of the tube wall increases only in direct proportion to the diameter of the tube. Thus, inadequate cooling may occur and this results in an elevated reaction temperature, which in turn causes unacceptable variation of the color of the reaction product. Likewise the thickness of the liquid film essentially increases in proportion to the tube diameter whereby unequal distributions of reactant concentration and temperature are generated inside the liquid film, thereby creating unstable conditions and making it difficult to minimize unwanted side-reactions.

SUMMARY OF THE INVENTION

The present invention relates to an apparatus for sulfonation which can be effectively employed for large-scale production of sulfonated compounds. Although the present invention is similar to the conventional procedure in the feature that the reaction is performed as a two-stage reaction, the present invention obtains unexpectedly improved results by carrying out the first-stage reaction in a plurality of reaction tubes in a parallel arrangement and conducting the second-stage reaction in a single reaction tube.

The advantage brought about by the use of plural reaction tubes for the first-stage reaction is as follows. Namely, because the reaction is not 100% completed (on the basis of the organic compound fed in) in the first-stage reaction, the molar ratio between the liquid and gas fed into each of the first-stage reactors need not be controlled precisely. That is to say, a precise liquid-gas ratio control can be effected on the combination of the first-stage and second-stage reaction, as a whole, but a strict control of each reaction stage and of each reactor of the first stage is not necessary. For example, when the reaction is carried out to about 80% completion in the first-stage and the balance of the reaction (about 20%) is completed in the second-stage, the degree of reaction completion in each of the first-stage reactors can be different, such as 78% in one first-stage reactor and 82% in another first-stage reactor. Because the reaction products from the individual first-stage reactors are combined and the mixture as a whole is subjected to completion of the reaction in the subsequent second-stage reactor, non-uniformity in the degrees of completion of the reaction in the individual first-stage reactors does not give an adverse effect on the quality and other properties of the resulting final product.

On the other hand, the sulfonation reaction is a highly exothermic reaction and the efficiency of cooling exerts a significant influence on the color of the final product. However, it is obvious from the engineering point of view that the cooling effect is reduced when the diameter of the tube is increased because the increase in the flow quantity is larger than the increase in the heat transfer area of the wall of the tube. The present invention employs reaction tubes of relatively small diameter for the first-stage reaction, where the reaction is relatively rapid, in order to ensure adequate cooling and thus effectively minimizes coloring that might otherwise occur due to the occurrence of excessively high temperatures.

An embodiment of the reaction apparatus in accordance with the present invention will be described with reference to the accompanying drawings.

BRIEF DESCRIPTION OF THE DRAWINGS

As shown in FIG. 1, three vertical tubes, 1, 2, 3 are concentrically disposed to define an outer annular space between tubes 2 and 3, and an inner annular space between tubes 1 and 2. A number of vertical first-stage reaction tubes 4 are disposed in the annular space between the tubes 2 and 3 at a predetermined distance from the center of tube 1 and with identical spacings between each other. The tubes 4 are secured at their upper and lower ends to tube plates 5 and 6. The tube plate 6 has an annular conduit section 7 extending axially from the lower end of each of the tube 4 and another conduit section 8 which extends at right angles to the conduit section 7. An upright nozzle 9 is positioned in the conduit 7 and extends upwardly into the lower end of the tube 4. The nozzle 9 is substantially concentric with the tube 4 and communicates therewith.

Figure 1:
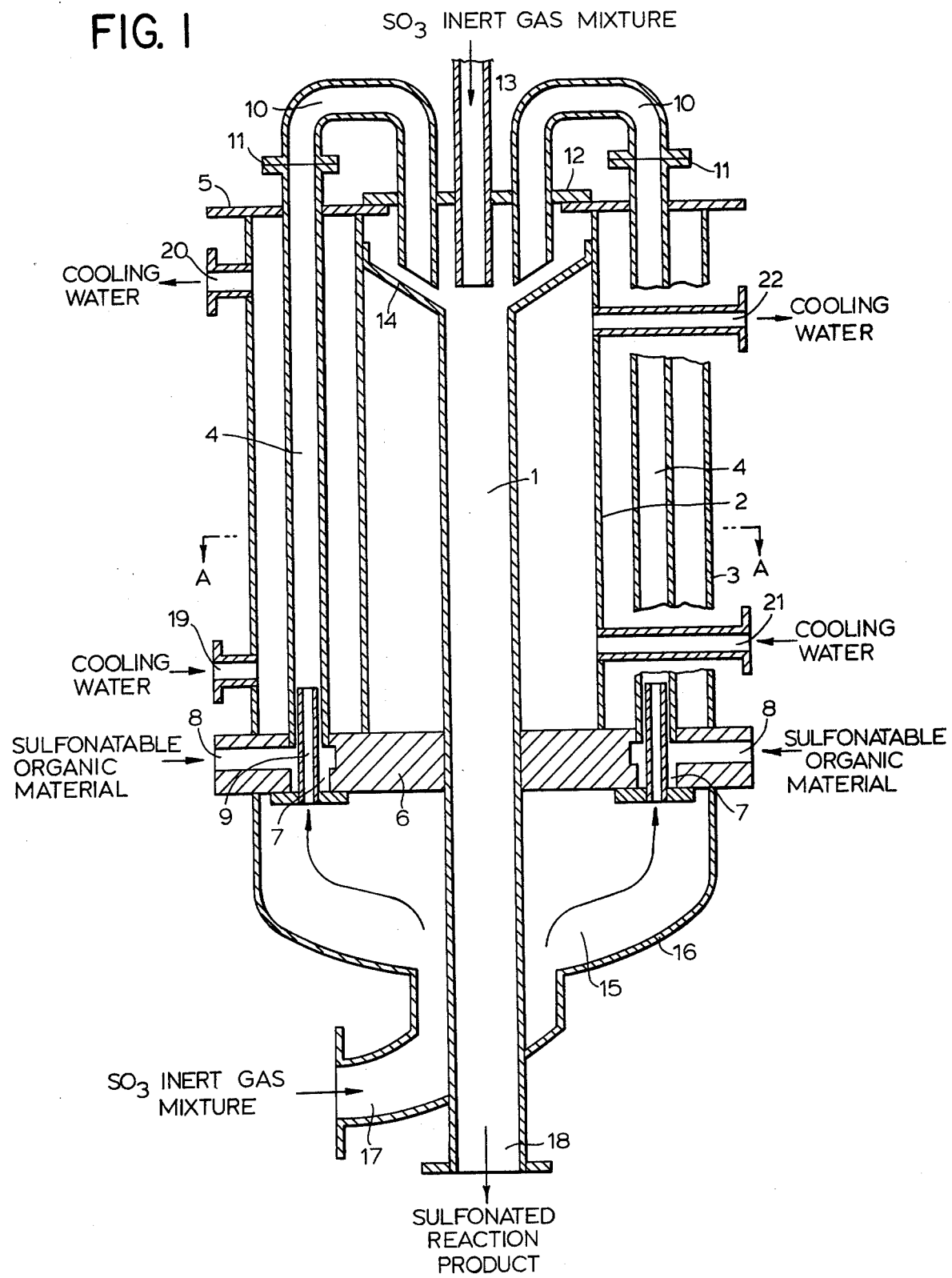
FIG. 1 is a longitudinal central sectional view of one embodiment of an apparatus according to the present invention.

Thus, there are provided two paths communicating with the inside of the tube 4. One path passes through the inside of the nozzle 9 from below the tube plate 6 and the other passes through the conduit section 8 from the side surface of the tube plate 6 and through the annular space defined between the tube 4 and the nozzle 9.

A reversely curved tube 10 is joined at one end thereof to the upper end of the tube 4 by a flange 11 and the other end of the tube 10 extends downwardly through a cover plate 12. The cover plate 12 closes a central opening in the tube plate 5. A nozzle 13 extends downwardly through the cover plate 12 at the center thereof. The upper end of the tube 1 has an inverted frusto-conical liquid-collection section 14, the upper end of which is joined to the inner wall of the tube 2. To the lower end of the tube plate 6, there is secured a dome-shaped end plate 16 so as to define a space 15 therebetween. An inlet conduit 17 is connected to the lower end of the end plate 16. The lower portion of the tube 1 penetrates through the tube plate 6 as well as the end plate 16 and it has a discharge port 18.

One or more intake nozzles 19 for cooling water and discharge nozzles 20 for cooling water are attached to the tube 3. One or more intake nozzles 21 for cooling water and discharge nozzles 22 for cooling water are similarly attached to the tube 2. Thus, the exterior surfaces of tubes 4 and tube 1 are cooled by the cooling water supplied through the nozzles.

Figure 2:
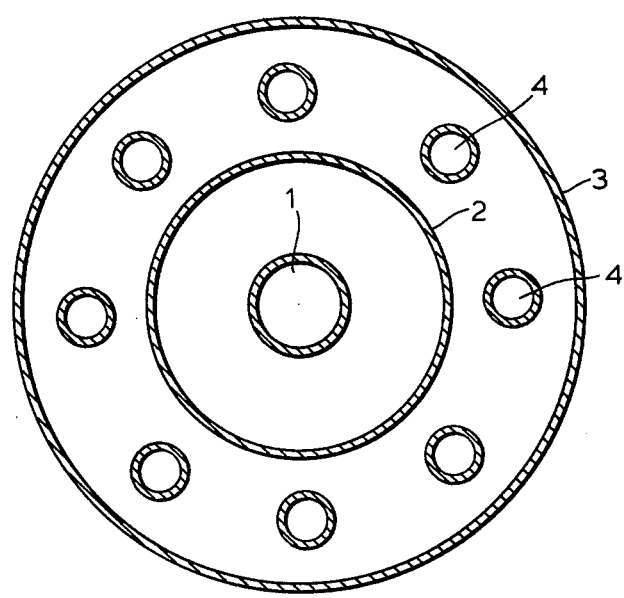
FIG. 2 is a sectional view taken on the line A—A of FIG. 1.

As can be seen from FIG. 2, the above-mentioned embodiment uses eight tubes 4. Needless to say, the number of the tubes 4 can be changed as desired. Likewise, the method of connecting the nozzles and the like can be changed.

The apparatus of the present invention explained above is operated in the following manner.

A predetermined quantity of a liquid organic compound is fed to each of the conduits 8 by a metering pump or like means. Since the apparatus shown in FIGS. 1 and 2 has eight tubes 4, it also has eight conduits 8. Hence, the starting sulfonatable compound is continuously fed in a predetermined metered quantity to each of the eight tubes 4. A SO$_3$-containing gas is fed in through the nozzle 17. The SO$_3$-containing gas flows into each of the tubes 4 through the nozzles 9. The gas aspirates the organic compound rising through the space between the nozzle 9 and the tube 4 and rises upwardly, and forms a rising thin film of the organic compound on the inner wall of the tube 4.

The operation of the tubes 4 is described more fully in U.S. Pat. application Ser. No. 243,874, filed Apr. 13, 1972, the entire contents of which are incorporated herein by reference.

The organic compound discharged via the curved tube 10 (that is to say, the incompletely sulfonated product) is collected by the liquid-collection device 14 and thence flows downwardly along the inner wall of the single tube 1 in the form of a thin film. The gas discharged from the curved tube 10, on the other hand, flows downwardly inside the tube 1 together with fresh SO$_3$-containing gas that is fed in from the nozzle 13. The substantially completely sulfonated organic compound and the gas are discharged from the lower port 18. The mixture of the organic compound thus discharged (sulfonated product) and the gas is subjected to the gas-liquid separation by a cyclone or like means and then the sulfonated product is neutralized to obtain a final product. The gas-liquid separation and the neutralizing step can be of any suitable, customary type and these are not illustrated in the accompanying drawings.

Since the sulfonation reaction is an exothermic reaction, cooling water is introduced from the nozzle 19 thereby to prevent an excessive increase of the temperature of the organic compound undergoing the first-stage reaction inside the tubes 4. In the second-stage reaction inside the tube 1, on the other hand, the occurrence of an excessive temperature increase of the organic compound is likewise prevented by introducing cooling water from the nozzle 21. The nozzles 20 and 22 are provided for discharging the cooling water. The system of supplying the cooling water is not specifically limited to the above-mentioned arrangement. For example, the cooling water can be introduced from the nozzle 20 and discharged from the nozzle 19. When the tubes 1 and 4 have a considerably long length, for example, plural feed and discharge ports can be provided for the cooling water.

In the first-stage reaction in accordance with the present invention, the starting material for the reaction, plus an air or an inert gas stream containing 1 to 20% by volume of sulfur trioxide (SO$_3$), are fed continuously from below upwardly into the vertical tubes 4. The gas stream velocity inside the tubes 4 is selected to be more than 20 m/sec. so that the gas per se acts as a driving force, forms a rising annular film of the organic sulfonatable material inside the reaction tube 4 and thus ensures sufficient mixing of the reactants and cooling of the reaction mixture on the inner wall surface of the tube. Since the rising annular film is elevated against the effect of gravity, it undergoes mixing and thus minimizes undesirable side-reactions.

When the gas velocity in the tubes 4 exceeds 120 m/sec. the liquid film is agitated in an extremely vigorous fashion, thereby to form a mist of the liquid dispersed in the gas. In consequence, the gas-liquid contact becomes undesirably excessive whereby the reaction speed also becomes excessively rapid and the reaction heat uncontrollably high. In addition, the pressure loss also increases and this results in economic disadvantages. Thus, the maximum gas velocity in the tubes 4 is 120 m/sec.

The gas-liquid contact is initiated at the point where the gas stream is jetted out from the nozzle 9. Alternatively the liquid starting organic material can be jetted together with an inert gas thereby to form a rising annular film inside the reaction tube, following which a second gaseous stream of the SO$_3$ gas or a mixture gas containing a high concentration of SO$_3$ can be introduced and brought into contact with the liquid. See U.S. Pat. No. 2,923,728 which illustrates this technique.

The conditions for forming the rising annular film vary depending upon the properties of the reactants, i.e., the organic starting material, as well as the SO$_3$-inert gas mixture and the properties of the intermediate materials. In the case of the starting material used in the present invention as will be hereinafter described, the annular rising film can be formed when the gas velocity is in the range of 20 to 120 m/sec.

In this instance, the annular film does not rise in a simple laminar flow along with the wall of the tube. On the contrary, the reaction mixture liquid rises upwardly while undergoing a revolving flow so as to moderately agitate the film and peel portions of the film off the wall surface to expose fresh reaction surfaces but without destroying the film as a whole.

The first-stage reaction is of utmost importance for controlling coloring of the product. In the present invention, this first-stage reaction is carried out by means of the rising film while adequate cooling is ensured by a plurality of tubes disposed in parallel arrangement, with the consequence being that the resulting sulfonated product is of an extremely good quality. The second-stage reaction, on the other hand, is effected primarily to complete the reaction. Hence, no problem such as inadequate cooling and the like occurs when the reaction is carried out by means of a single falling film in tube 1. Likewise, because the flow of the liquid reactant in the second-stage is helped by gravity, the velocity of the gas stream in tube 1 is not critical.

The degree of completion of the reaction in the first-stage reaction is in the range of 60 to 95%, preferably in the range of 75 to 95%, and the remainder of the reaction is completed in the second-stage. The quantity of the $SO_3$-containing gas supplied via conduit 17, in proportion to the organic compound supplied by conduits 8 in the first-stage reaction, is selected properly so as to satisfy the above-mentioned degree of completion of the reaction in the first stage.

The proportion of the organic compound to the total $SO_3$ supplied to the whole reaction system, including the first-stage and second-stage reactions, is preferably controlled so that the amount of $SO_3$ is from 1.0 to 1.1 mole of the organic compound.

The diameter of tube 1 is larger than the diameters of tubes 4 so that the combined liquid streams from tubes 4 will flow downwardly along the tube 1 as a thin film. The film that flows along tube 1 can be thicker than the films that flow along tubes 4. For example the films that flow upwardly on tubes 4 can have a thickness of 0.012 to 0.12 cm and the film that flows downwardly on tube 1 can have a thickness of up to about 0.5 cm.

The compounds that are sulfonated in the present invention are the conventional sulfonatable and sulfatable materials that are liquid at ordinary or reaction temperatures (i.e., from about 10° to 125° C) and include the following:

1. Straight-chain or branched-chain alcohols having 8 to 20 carbon atoms, and mixtures of these alcohols.
2. Alkyl benzenes having an alkyl side chain of 0 to 25 carbon atoms, and mixtures thereof.
3. Straight-chain olefins having 6 to 25 carbon atoms, and mixtures thereof.
4. Adducts of alkylene oxides and active hydrogen compounds such as alcohols, phenols or fatty acids.
5. Alkylolamides of fatty acids having 10 to 20 carbon atoms.
6. Fatty acids having 8 to 20 carbon atoms and mixtures thereof, and lower alcohol esters of these fatty acids and mixtures of these lower alcohol esters.
7. Polyhydric alcohol esters of fatty acids having 8 to 20 carbon atoms and alkylene oxide adducts thereof.

The above-mentioned compounds of the classes 1 through 7 can be mixed if desired and the mixture can be subjected to the sulfonation reaction in the present invention.

As an example of the $SO_3$-containing gas, mention can be made of stabilized sulfuric anhydride (e.g. "Sulfan", a trade name) which is first evaporated and then diluted with air or an inert gas, or a so-called converter gas obtained by converting a combustion gas of sulfur, which is used either as such or after dilution. The $SO_3$ concentration in the $SO_3$-containing gas is from 1 to 20% by volume, preferably from 2 to 10% by volume.

EXAMPLE

Sulfonation is carried out using the apparatus of the type shown in the drawing wherein 8 tubes of an inner diameter of 25 mm and a length of 3 m are used for the first-stage reaction, and a single tube of an inner diameter of 81 mm and a length of 8 m (including a 5 m piping-arrangement extending below plate 6 for connection to a cyclone) is used for the second-stage reaction.

The results are illustrated in the table below.

For comparison, the results of two experiments are also illustrated wherein the reaction is terminated after only the first-stage reaction (Comparative 1) and wherein the rising thin film reaction is carried out by the use of a single tube having an inner diameter of 90 mm and a length of 30 m (Comparative 2).

|  | This invention | Comparative 1 | Comparative 2 |
|---|---|---|---|
| Lauryl alcohol |  |  |  |
| Flow Quantity (kg/hr) | 245 | 245 | 178 |
| $SO_3$ + air |  |  |  |
| Flow Quantity (NM³/hr) | 1164 | 1164 | 1075 |
| $SO_3$ concentration % | 2.32 | 2.32 | 1.81 |
| Distribution ratio of $SO_3$ first-stage/second-stage | 84/16 | — | — |
| Reaction rate % | 96.8 | 96.7 | 96.5 |
| Reaction product (neutralized product) color, Klett number | 10 | 52 | 40 |
| Lauroxypolyethoxy ethanol (M.W. 320) |  |  |  |
| Flow Quantity (kg/hr) | 237 | 237 | 278 |
| $SO_3$ + Air |  |  |  |
| Flow Quantity (NM³/hr) | 905 | 905 | 1075 |
| $SO_3$ concentration % | 1.80 | 1.80 | 1.78 |
| Distribution ratio of $SO_3$ first-stage/second-stage | 80/20 | — | — |
| Reaction rate % | 96.7 | 96.4 | 95.2 |
| Reaction product (neutralized product) color, Klett number | 31 | 73 | 50 |

REMARKS

The Klett number is obtained in the following manner. The reaction product is neutralized and adjusted to an aqueous solution containing 10% of sulfonated component. The absorption at 420 mµ in a 1 cm cell is multiplied by 1000 to give the Klett number.

The embodiments of the invention in which an exclusive property or privilege is claimed are defined as follows:

1. An apparatus for reacting a liquid organic reactant with sulfur trioxide gas, comprising:
   a plurality of individual, parallel, vertically positioned, hollow, cylindrical, first-stage reaction tubes, each of said tubes being of circular cross-section and each of said tubes having at the lower end thereof a central inlet for feeding a stream of a mixture of sulfur trioxide gas and inert gas upwardly into the central region of the tube at the lower end thereof and an outer annular inlet surrounding said central inlet and isolated therefrom for feeding an annular stream of said liquid organic reactant upwardly onto the circular internal wall of the tube at the lower end thereof, said inlets for each tube terminating adjacent the lower end of the tube and the remainder of the tube being open to permit concurrent, upward, parallel flow and contact between said streams to effect the reaction whereby in each of said reaction tubes an annular rising thin film of said liquid organic reactant is formed on the tube wall by said gas stream and the sulfur trioxide in said gas stream reacts with said liquid organic reactant;

means for cooling the external surface of each of said first-stage reaction tubes along substantially the entire length thereof to remove the exothermic heat of reaction generated therein by reaction between said organic reactant and said sulfur trioxide;

a single, vertically positioned, hollow, cylindrical, second-stage reaction tube of circular cross-section having an inlet at the upper end thereof, an outlet at the lower end thereof and means for cooling the external surface of said second-stage reaction tube along the length thereof to remove the exothermic heat of reaction generated therein;

each of said first-stage reaction tubes having a conduit extending from the upper end thereof to the inlet of said second-stage reaction tube so that the entireties of the gas and liquid streams exiting from all of the first-stage reaction tubes are fed into the inlet of said second-stage reaction tube and are combined therein;

and a further inlet pipe extending to the central portion of the inlet of said second-stage reaction tube for supplying thereto an additional, downwardly flowing stream of a mixture of sulfur trioxide gas and inert gas, whereby the combined liquid streams from all of said first-stage reaction tubes form an annular falling thin film on the wall of said second-stage reaction tube and the sulfur trioxide gas in said additional stream reacts with previously unreacted liquid organic reactant to complete the sulfonation thereof.

2. An apparatus as claimed in claim 1 in which said second-stage reaction tube has an inverted frusto-conical collecting receptacle at the upper end thereof, said conduits from said first-stage reaction tubes all opening downwardly into said collecting receptacle and the inlet of said second-stage reaction tube being located at the lower central portion of said collecting receptacle.

3. An apparatus as claimed in claim 1 including three concentric tubes, the innermost one of said tubes defining said second-stage reaction tube, the space between the innermost tube and the intermediate tube defining a first zone for containing a coolant and means for supplying coolant to and removing coolant from said first zone, the space between said intermediate tube and the outer tube defining a second zone for containing a coolant and means for supplying coolant to and removing coolant from said second zone, said first-stage reaction tubes being positioned in said second zone spaced from the intermediate and outer tubes and in circumferentially spaced relation to each other, and closure plate means closing the upper and lower ends of said first and second zones.

4. An apparatus as claimed in claim 1 wherein said conduits from said first-stage reaction tubes are reversely curved conduits that extend radially inwardly and then downwardly to communicate with the inlet at the upper end of said second-stage reaction tube.

5. A sulfonation apparatus, comprising:

a plurality of individual, parallel, vertical, externally cooled, first-stage reaction tubes, each of said tubes having at the lower end thereof inlet port means for feeding upwardly into the lower end of the tube a stream of a mixture of sulfur trioxide gas and inert gas and a stream of liquid organic reactant so that said liquid organic reactant forms a thin rising film on the internal wall of the tube, said thin rising film of said liquid organic reactant surrounding said stream of said mixture of gases for reactive contact with the sulfur trioxide in said mixture of gases as the liquid and gas flow upwardly through the tube in concurrent, upward, parallel, flow relationship;

a single, vertical, externally cooled, second-stage reaction tube arranged in parallel with said first-stage reaction tubes, said second-stage reaction tube having liquid collecting means at the upper end thereof and an outlet at the lower end thereof;

conduits extending from the upper ends of all of said first-stage reaction tubes to said liquid collection means of said second-stage reaction tube for feeding the liquids and gases leaving the upper ends of said first-stage reaction tubes into said liquid collection means to combine the liquids and to feed the combined liquids into the upper end of said second-stage reaction tube to form a falling film of the combined liquids on the internal wall of said second-stage reaction tube;

and a feed port extending to the central portion of the upper end of said second-stage reaction tube for feeding downwardly into the upper end of said second-stage reaction tube an additional stream of a mixture of sulfur trioxide gas and inert gas which additional stream flows downwardly through said second-stage reaction tube in concurrent, downward, parallel flow relationship with said combined liquids, and the sulfur trioxide gas in said additional stream reacts with previously unreacted liquid organic reactant to complete the sulfonation thereof.

6. A sulfonation apparatus as claimed in claim 5 in which said first-stage reaction tubes and said second-stage reaction tube have circular cross sections and the diameter of said second-stage reaction tube is larger than the diameters of said first-stage reaction tubes.

7. A sulfonation apparatus as claimed in claim 5 in which said first-stage reaction tubes are arranged in a circular array and said second-stage reaction tube is located at the center of the circular array.

* * * * *